(12) United States Patent
Justis

(10) Patent No.: US 6,273,888 B1
(45) Date of Patent: Aug. 14, 2001

(54) DEVICE AND METHOD FOR SELECTIVELY PREVENTING THE LOCKING OF A SHAPE-MEMORY ALLOY COUPLING SYSTEM

(75) Inventor: Jeff R. Justis, Cordova, TN (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/407,431

(22) Filed: Sep. 29, 1999

Related U.S. Application Data
(60) Provisional application No. 60/136,678, filed on May 28, 1999.

(51) Int. Cl.⁷ .............................. A61B 17/68; A61B 17/70
(52) U.S. Cl. .................................................. 606/61; 606/60
(58) Field of Search ................... 606/60, 61, 72, 606/73, 78, 69; 411/433

(56) References Cited

U.S. PATENT DOCUMENTS

| | | | |
|---|---|---|---|
| 4,379,575 | 4/1983 | Martin | 285/369 |
| 4,665,906 | 5/1987 | Jervis | 128/92 YN |
| 4,946,458 * | 8/1990 | Harms et al. | 606/61 |
| 5,160,233 | 11/1992 | McKinnis | 411/433 |
| 5,366,331 | 11/1994 | Erbes | 411/433 |
| 5,380,323 * | 1/1995 | Howland | 606/61 |
| 5,433,467 | 7/1995 | Biedermann et al. | 606/65 |
| 5,551,871 | 9/1996 | Besselink et al. | 433/5 |
| 5,578,034 * | 11/1996 | Estes | 606/61 |
| 5,586,984 | 12/1996 | Errico et al. | 606/61 |
| 5,597,378 | 1/1997 | Jervis | 606/78 |
| 5,669,911 * | 9/1997 | Errico et al. | 606/61 |
| 5,683,404 | 11/1997 | Johnson | 606/151 |
| 5,716,356 * | 2/1998 | Biedermann et al. | 606/61 |
| 5,728,098 | 3/1998 | Sherman et al. | 606/61 |
| 5,733,285 * | 3/1998 | Errico et al. | 606/61 |
| 5,810,818 * | 9/1998 | Errico et al. | 606/61 |
| 5,885,286 * | 3/1999 | Sherman et al. | 606/61 |
| 5,961,516 * | 10/1999 | Graf | 606/61 |
| 5,961,517 * | 10/1999 | Biedermann et al. | 606/61 |
| 6,053,917 * | 4/2000 | Sherman et al. | 606/61 |
| 6,086,608 * | 7/2000 | Ek et al. | 606/232 |
| 6,171,311 * | 1/2001 | Richelsoph | 606/61 |

OTHER PUBLICATIONS

"Some Applications of Shape–Memory Alloys", *Journal of Metals*, Jun., 1980, by C.M. Wayman, University of Illinois at Urbana–Champaign, Urbana, Illinois.

* cited by examiner

*Primary Examiner*—Paul J. Hirsch
*Assistant Examiner*—Michael B. Priddy
(74) *Attorney, Agent, or Firm*—Woodard, Emhardt, Naughton, Moriarty & McNett

(57) ABSTRACT

A shape-memory alloy coupling system for connecting two or more members and selectively preventing premature locking. The coupling system includes a coupling device adapted for connection to a member and being at least partially formed of a shape-memory material. The coupling device has a first configuration that allows relative movement between the member and the coupling device, and a second configuration that limits relative movement between the member and the coupling device. A blocking element co-acts with the coupling device to selectively prevent the coupling device from assuming the second configuration.

35 Claims, 4 Drawing Sheets

DEVICE AND METHOD FOR SELECTIVELY PREVENTING THE LOCKING OF A SHAPE-MEMORY ALLOY COUPLING SYSTEM

This application is based on provisional patent application Ser. No. 60/136,678, filed May 28, 1999, and priority is claimed in the present application to the extent the subject matter of this application is found in that provisional application. The content of that application is incorporated herein by reference.

FIELD OF THE INVENTION

The present invention broadly concerns a coupling system using shape-memory technology. Specifically, the invention concerns a device and method for selectively preventing the locking of a shape-memory alloy coupling system, preferably in environments above the transformation temperature of the shape-memory material.

BACKGROUND OF THE INVENTION

Several techniques and systems have been developed for correcting and stabilizing the spine and for facilitating fusion at various levels of the spinal column. One form of a spinal fixation system utilizes bendable spinal rods situated on opposite sides of the spine and coupled to a plurality of fixation elements, which are in turn attached to various portions of the spine. One such system is described in U.S. patent application Ser. No. 09/408,197, entitled "Advanced Coupling Device Using Shape-Memory Technology" and filed on the same day as the subject application, which is hereinafter incorporated by reference. This particular system includes a coupling element defining a longitudinal passage therethrough and having a side wall defining first and second slots extending from opposite ends thereof and including proximately adjacent and longitudinally overlapping portions. A locking element at least partially formed of a shape-memory material is positioned about the coupling element and, upon a sufficient change in temperature, contracts about the coupling element and compresses the side wall against a member disposed within the longitudinal passage to limit movement of the member relative to the coupling element.

Shape-memory materials are alloys of known metals, such as, for example, copper and zinc, nickel and titanium, and silver and cadmium. These alloys are known to exhibit a "shape-memory" characteristic in which a particular component formed of a shape-memory alloy ("SMA") is capable of reforming to a "memorized" shape upon a sufficient change in temperature. Such components are originally deformed from an initial configuration and retain their deformed configuration until they are sufficiently heated, at which point they begin to recover toward their original, memorized configuration. This recovery phenomena occurs when the SMA alloy changes from a martensitic crystal phase to an austenitic crystal phase. SMAs thus exhibit a memory effect upon passing from a low temperature form (e.g. martensitic stage) to a high temperature form (e.g., austenitic stage).

When an SMA is heated, transformation toward the original, memorized shape occurs over the range $A_s$–$A_f$, where $A_s$ and $A_f$ are the temperatures at which formation of austenite begins and is completed, respectively. Conversely, when an SMA is cooled, transformation back toward the deformed shape occurs over the range of temperatures $M_s$–$M_f$, where $M_s$ and $M_f$ are the temperatures at which formation of martensite begins and is completed, respectively. For many SMAs, $A_s$ and $M_s$ are approximately the same and therefore shape transformation begins at about the same temperature, independent of whether the SMA is being heated or cooled.

In certain medical applications, it is often beneficial to choose a SMA having an $A_f$ temperature less than normal body temperature to avoid having to provide external means for applying heat to raise the temperature of the SMA above $A_f$. Additionally, because it is necessary for the SMA to remain in the austenitic state during use (i.e., to avoid possible re-expansion of a SMA coupling device which may result in the loosening of clamping forces), the $M_s$ of the SMA is preferably somewhat lower than the lowest temperature which the SMA will encounter during use. It is therefore advantageous to choose a SMA with relatively low $A_f$ and $M_s$ temperatures to: 1.) ensure that the maximum stress is recovered from the SMA by completely transforming the shape-memory material to its austenitic state, and 2.) avoid potential problems which may result if the temperature of the SMA drops below the $M_s$ temperature. However, by choosing an SMA with a relatively low $A_f$ temperature, there is a risk that the SMA will become sufficiently heated before or during installation so as to result in the premature transformation of the SMA into the austenitic state (i.e., the premature locking of a SMA coupling device before or during a surgical procedure). In the past, this typically required providing an external cooling means to maintain the temperature of the SMA below $A_f$ before and during installation of the shape-memory device.

In some applications of shape-memory alloys, mechanically constrained shape change may be preferable over heat actuated shape change. Mechanically constrained shape change employs the unique characteristics associated with stress-induced martensite, which does not require a change in temperature to effect reformation of the shape-memory material toward its original, memorized configuration. A mechanical restraint is initially used to hold the shape-memory alloy material in its deformed configuration (in a stress-induced martensitic state) until such a time when the restraint is removed, thus allowing the shape-memory alloy to reform toward its original, memorized configuration without a change in temperature. The use of stress-induced martensite (utilizing mechanically constrained shape change) in place of conventional shape memory alloy materials (utilizing heat actuated shape change) often offers a greater degree of control over the reformation of the shape-memory material. Stress-induced martensite also offers easier alloy composition control, reduces mating part tolerance requirements, and simplifies mechanical reversal at minimal stress levels. Further details regarding the use and characteristics of stress-induced martensite are more fully described in U.S. Pat. No. 5,597,378 to Jervis, entitled "Medical Devices Incorporating SIM Alloy Elements", which is hereinafter incorporated by reference into the subject application.

Thus, there is a general need in the industry to provide a device and method which selectively prevents the locking of a shape-memory alloy coupling system and allows for manipulation of the coupling system. The present invention meets this need and provides other benefits and advantages in a novel and unobvious manner.

SUMMARY OF THE INVENTION

The present invention relates generally to a coupling system using shape-memory technology. While the actual nature of the invention covered herein can only be determined with reference to the claims appended hereto, certain forms of the invention that are characteristic of the preferred embodiments disclosed herein are described briefly as follows.

In one form of the present invention, a coupling system is provided which includes a coupling device adapted for connection to a member and being at least partially formed of a shape-memory material to allow reformation of the device from a first configuration to a second configuration, with the first configuration allowing relative movement between the member and the coupling device and the second configuration limiting relative movement between the member and the coupling device. A blocking element co-acts with the coupling device to selectively prevent the coupling device from being reformed to the second configuration.

In another form of the present invention, a coupling system is provided which includes a connecting device adapted for connection to a member and being at least partially formed of a shape-memory material. The connecting device is capable of being reformed from one shape which allows relative movement between the member and the connecting device to a different shape which limits relative movement between the member and the connecting device. A restraining element is transitionable from a first state that prevents the connecting device from assuming the second shape to a second state that permits the coupling device to assume the second shape.

In yet another form of the present invention, a coupling system is provided for connection to a member, comprising a coupling element defining a passage sized to receive a portion of the member therein, a locking element formed at least partly of a shape-memory alloy and disposed about at least a portion of the coupling element, and a blocking element disposed within the passage. The locking element is capable of being reformed from a first configuration to a second configuration, with the first configuration co-acting with the coupling element to allow relative movement between the member and the coupling element, and the second configuration co-acting with the coupling element to limit relative movement between the member and said coupling element. The blocking element is transitionable between a first state and a second state, with the first state preventing the locking element from assuming its second configuration, and the second state permitting the coupling device to assume its second configuration.

In a further form of the present invention, a method is provided which includes providing a coupling device adapted to be connected to a member and being at least partially formed of a shape-memory material to allow reformation of the coupling device; providing a blocking element; preventing the coupling device from reforming through co-action between the coupling device and a first state of the blocking element to allow relative movement between the member and the coupling device; and transitioning the blocking element from the first state to a second state to permit reforming of the coupling device to limit relative movement between the member and the coupling device.

It is one object of the present invention to provide a coupling system using shape-memory technology.

Another object of the present invention is to provide a device and method for selectively preventing the locking of a shape-memory alloy coupling system.

Further objects, features, advantages, benefits, and aspects of the present invention will become apparent from the drawings and description contained herein.

DESCRIPTION OF THE PREFERRED EMBODIMENTS

Figure 1:
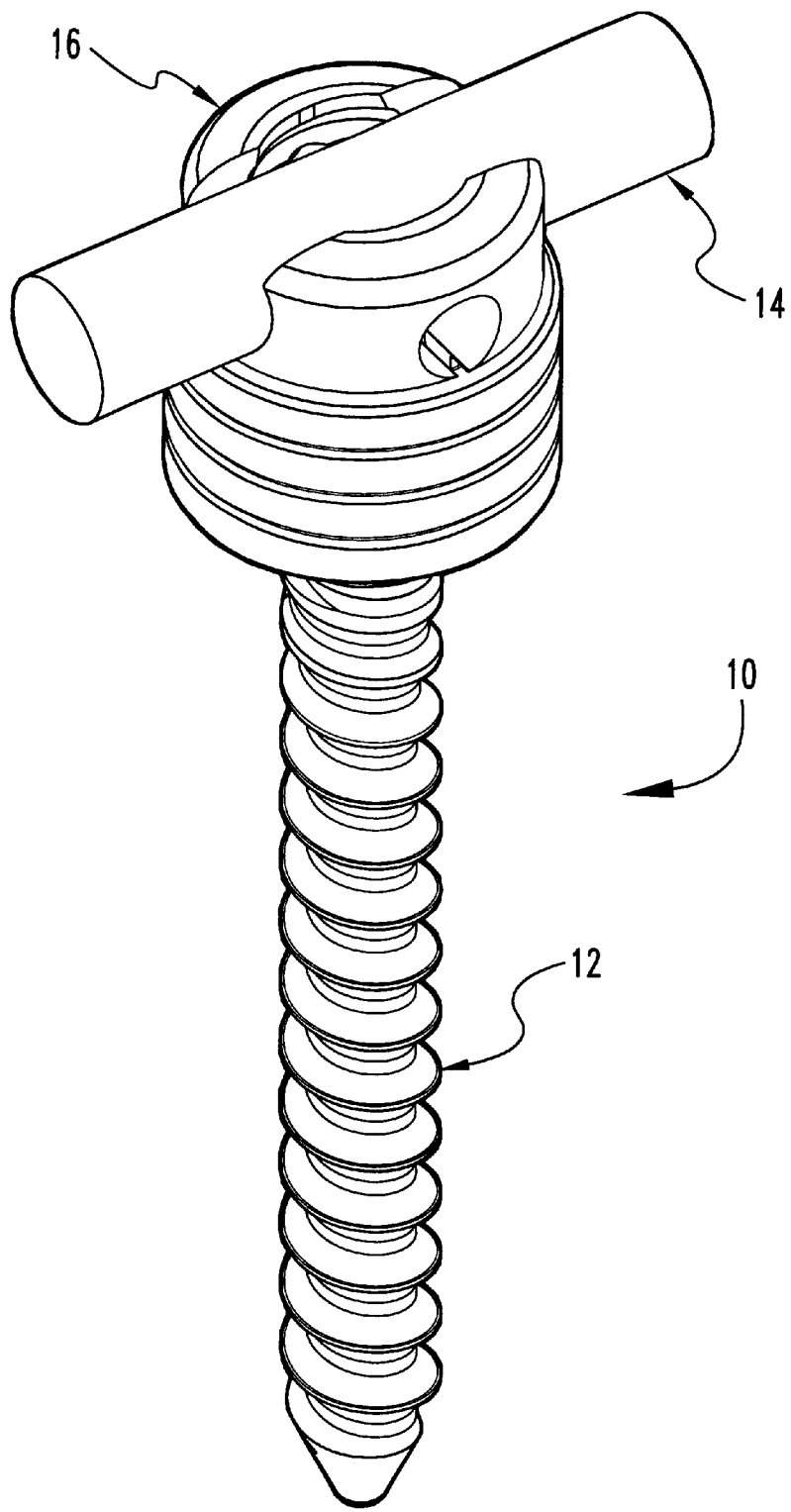
FIG. 1 is an side perspective view of a spinal fixation system according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, any alterations and further modifications in the illustrated device, and any further applications of the principles of the invention as illustrated herein being contemplated as would normally occur to one skilled in the art to which the invention relates.

FIG. 1 depicts a coupling system 10 according to a preferred embodiment of the present invention. Coupling system 10 generally includes a coupling device 16 and a blocking or restraining element 22. In a preferred embodiment, coupling system 10 is configured to connect a bone engaging member 12 to an elongate member 14. In one embodiment, bone engaging member 12 is a bone screw and elongate member 14 is a spinal rod. However, it should be understood that other configurations of bone engaging member 12 and elongate member 14 are also contemplated as being within the scope of the invention. For example, bone engaging member 12 could alternatively be a vertebral hook. In a preferred application of system 10, a pair of spinal rods 14 are situated on opposite sides of the spinal column, and a plurality of bone engaging screws 12 are attached to two or more vertebral bodies and affixed to spinal rod 14. It should also be understood that system 10 can be used to connect members having application outside of the spinal field. Further applications of system 10 are more fully disclosed in U.S. patent application Ser. No. 09/408,197, filed on the same day as the subject application and entitled "Advanced Coupling Device Using Shape-Memory Technology", which has been incorporated by reference into the subject application.

Figure 2:
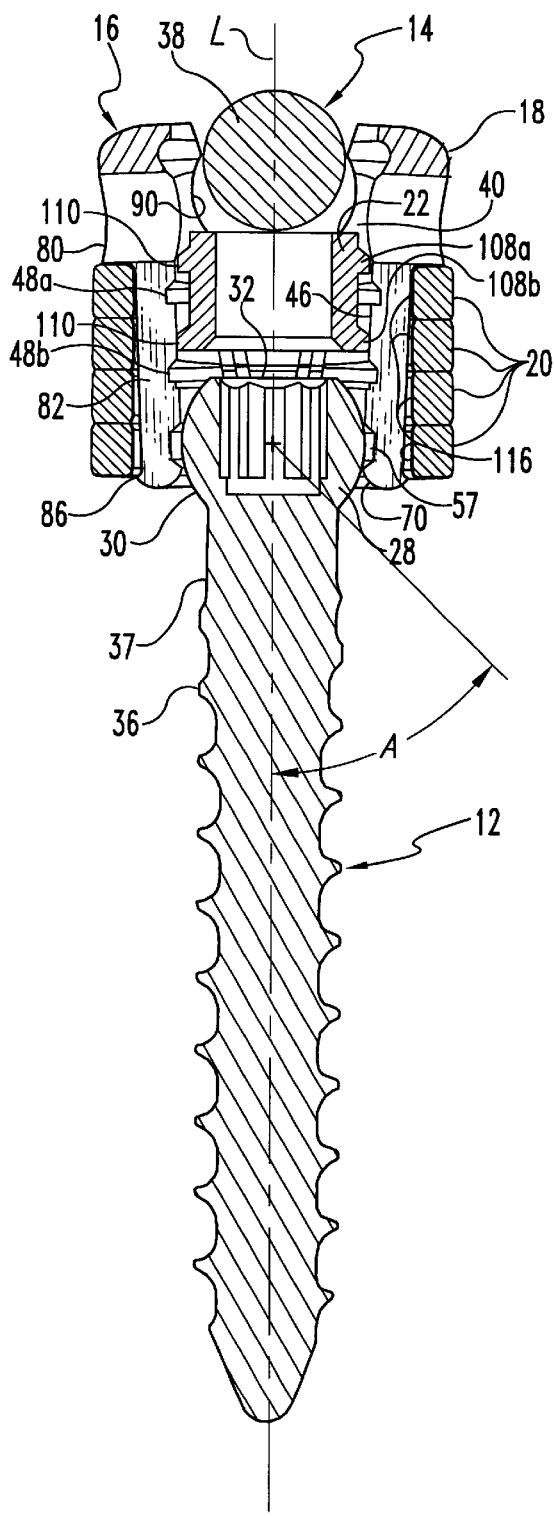
FIG. 2 is a side cross-sectional view of the system depicted in FIG. 1, showing the blocking element disposed within the coupling element in an engaged position.
Figure 3:
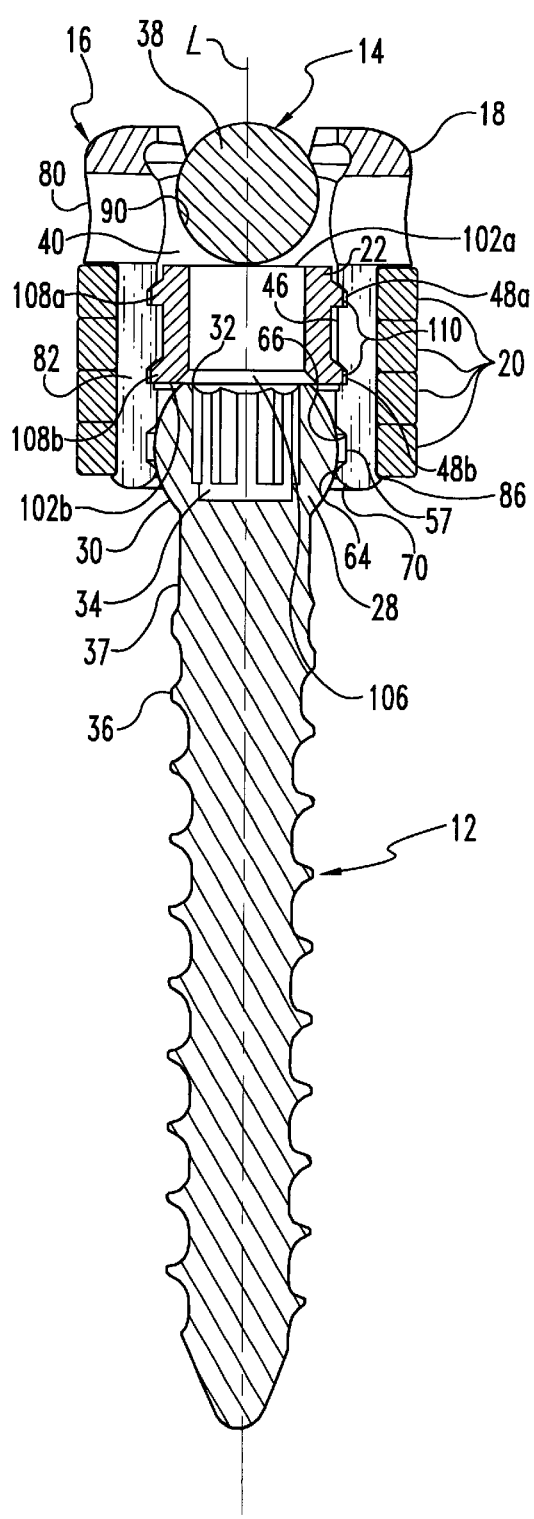
FIG. 3 is a side cross-sectional view of the system depicted in FIG. 1, showing the blocking element disposed within the coupling element in a disengaged position.

Referring now to FIGS. 2 and 3, bone screw 12 is shown connected to spinal rod 14 by way of coupling device 16. Coupling device 16 includes a coupling element 18 defining a longitudinal axis L, and a plurality of locking elements 20. Coupling element 18 is configured to receive portions of bone screw 12 and spinal rod 14 therein. Locking elements 20 are disposed about a portion of coupling element 18 and aligned generally along longitudinal axis L. Blocking element 22 is disposed within coupling element 18 and aligned generally along longitudinal axis L.

As illustrated in FIG. 2, in a first configuration of coupling device 16, blocking element 22 co-acts with coupling element 18 so as to prevent locking elements 20 from locking or clamping bone screw 12 and spinal rod 14 in a set position and orientation relative to coupling element 18. In this first configuration, bone screw 12 is allowed to freely rotate and pivot relative to coupling element 18, and spinal rod 14 is allowed to freely rotate and translate relative to coupling element 18. However, as illustrated in FIG. 3, in a second configuration of coupling device 16, blocking element 22 co-acts with coupling element 18 so as to allow locking elements 20 to lock or clamp bone screw 12 and spinal rod 14 in a set position and orientation relative to coupling element 18. In this second configuration, bone screw 12 is prevented from freely rotating and pivoting relative to coupling element 18, and spinal rod 14 is prevented from freely rotating and translating relative to coupling element 18. It can thus be seen that one purpose of blocking element 22 is to selectively prevent coupling device 16 from assuming its second configuration. Further details regarding the operation of coupling device 16 and blocking element 22 will be described more fully below.

Figure 4:
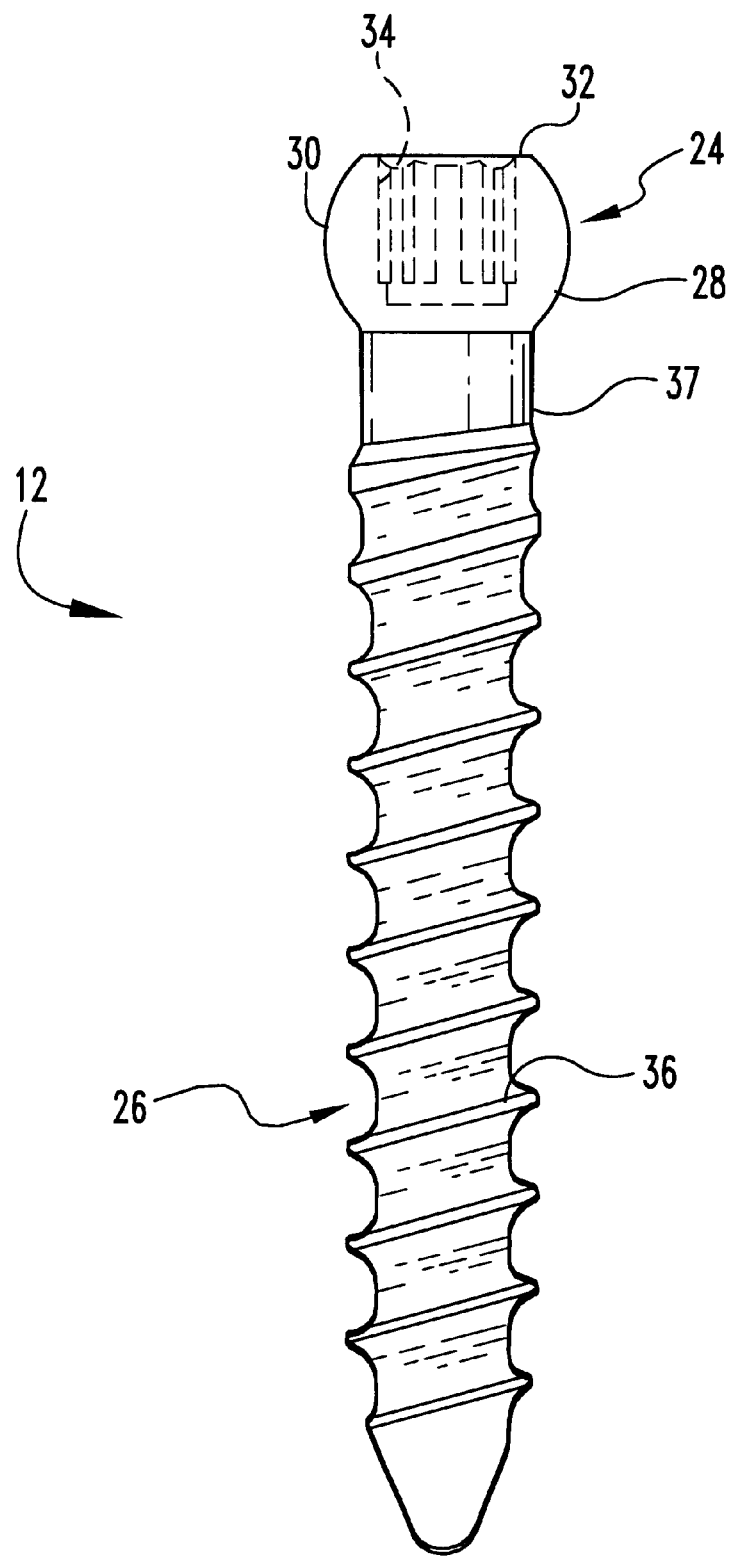
FIG. 4 is a side elevation view of one embodiment of a bone screw for use with the system depicted in FIG. 1.

Referring now to FIG. 4, shown therein are various structural details of bone screw 12. In one embodiment, bone screw 12 includes a connecting portion 24 and an engaging portion 26 extending therefrom. Preferably, connecting portion 24 includes an at least partially spherical-shaped head 28. Head 28 defines a substantially spherical surface 30 which cooperates with coupling element 18 to allow bone screw 12 to be aligned at a variety of angular orientations relative to longitudinal axis L. Although head 28 is shown to be substantially spherical-shaped, it should be understood that spherical surface 30 can take on a variety of shapes and configurations, such as an elliptical or arcuate shape.

In one specific embodiment of bone screw 12, head 28 includes a truncated, flat upper surface 32, through which is defined a tool receiving recess 34 that may be configured to accept any type of driving tool. Preferably, but not necessarily, tool receiving recess 34 is a hex recess sized to receive the hex end of a driving tool so that bone screw 12 may be driven into a vertebral body. Engaging portion 26 includes threads 36, which are preferably cancellous threads, configured to engage a vertebral body. Although engaging portion 26 is illustrated as being a threaded shank, it should be understood that engaging portion 26 can take on other configurations, such as a hook capable of engaging various aspects of a vertebral body. In a further aspect of bone screw 12, engaging portion 26 is provided with an unthreaded shank portion 37 extending between head 28 and cancellous threads 36.

Referring back to FIGS. 2 and 3, it can be seen that unthreaded shank portion 37 is configured to allow bone screw 12 to have a wider range of angular movement relative to longitudinal axis L by avoiding contact between cancellous threads 36 and the bottom end of coupling element 18 as bone screw 12 is pivoted relative to coupling element 18. In one embodiment, bone screw 12 is capable of assuming a wide range of angles, up to angle A, relative to longitudinal axis L. Although angle A is shown lying in a single plane (i.e., in the plane of the paper face), it should be understood that bone engaging member 12 is capable of pivoting through a generally conical path relative to longitudinal axis L. As also depicted in FIGS. 2 and 3, spinal rod 14 includes a connecting portion 38 having a generally circular, outer cross section. However, it should be understood that connecting portion 38 can take on a variety of alternative shapes, such as a square, an ellipse, or a number of other polygonal configurations.

Figure 6:
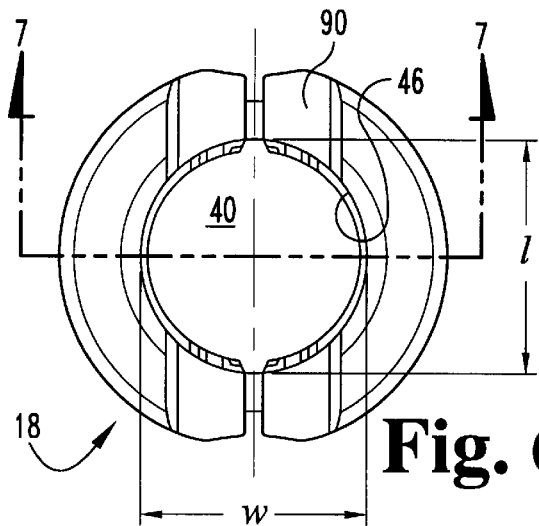
FIG. 6 is a top view of the coupling element shown in FIG. 5.
Figure 7:
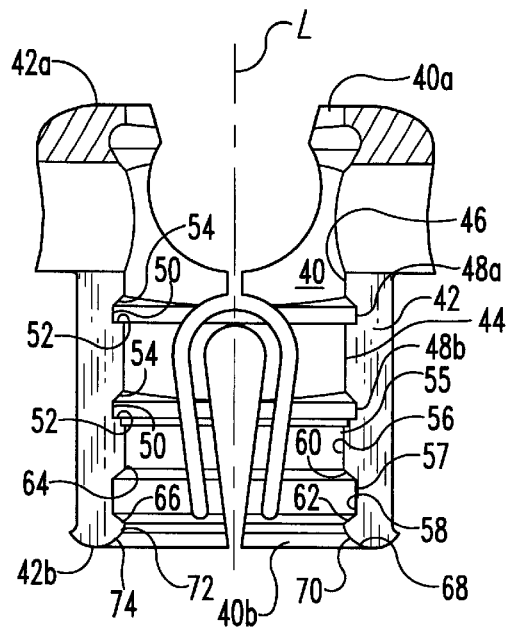
FIG. 7 is a side cross-sectional view of the coupling element shown in FIG. 5 taken along line 7—7 of FIG. 6.
Figure 5:
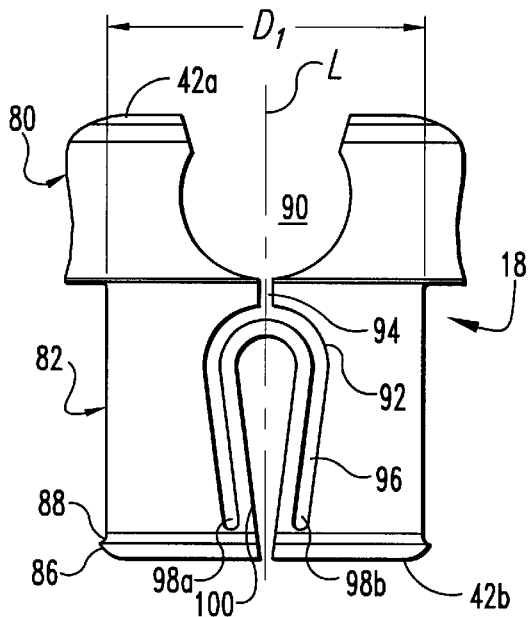
FIG. 5 is a side elevation view of one embodiment of a coupling element for use with the system depicted in FIG. 1.

Referring now to FIGS. 5–7, shown therein are various structural details of coupling element 18. Referring specifically to FIG. 7, coupling element 18 includes a passage 40 extending therethrough generally along longitudinal axis L, thus defining an upper opening 40a and a lower opening 40b. Longitudinal passage 40 is bounded by a side wall 42 having a first end 42a and an opposing second end 42b. Passage 40 is partially comprised of a slot 44, extending from first end 42a toward second end 42b. Slot 44 has an inner surface 46 defining a width w and a length l (FIG. 6). In one embodiment of coupling element 18, length l is slightly greater than width w. Alternatively, width w and length l may be substantially equal so as to define a generally circular bore. Passage 40 also includes a first radial recess or groove 48a and a second radial recess or groove 48b. First radial groove 48a is disposed along the depth of slot 44 between first end 42a and the end of slot 44. Groove 48a defines a circumferential surface 50, an annular surface 52, and a peripheral angular surface 54 serving as a transition between inner surface 46 of slot 44 and circumferential surface 50. Second radial groove 48b is disposed adjacent the end of slot 44 and is configured identically to first radial groove 48a. A generally circular bore 55, defining an inner surface 56, extends from second radial groove 48b toward second end 42b. Bore 55 transitions into a radial recess 57 having a circumferential surface 58, an upper peripheral angular surface 60, and a lower peripheral angular surface 62. Upper angular surface 60 serves as a transition between inner surface 56 of bore 55 and circumferential surface 58. The point at which upper angular surface 60 intersects inner surface 56 defines a generally circular upper edge 64. Similarly, lower angular surface 62 transitions into a generally conical bore 68 so as to define a generally circular lower edge 66. Conical bore 68 has an outwardly tapering inner surface 70, extending between lower angular surface 62 and second end 42b. Preferably, tapering inner surface 70 includes a generally flat angular surface 72, extending outwardly from lower angular surface 62 and transitioning into an outwardly extending arcuate surface 74, which in turn transitions into second end 42b. Although longitudinal passage 40 has been described as having a generally circular or oblong inner cross section, it should be understood that other shapes and configurations are also contemplated as being within the scope of the invention.

Referring specifically to FIG. 5, coupling element 18 includes a generally cylindrical-shaped upper portion 80 and a generally cylindrical-shaped lower portion 82. Lower portion 82 has an outer diameter $D_1$ that is preferably less than the outer diameter of upper portion 80. The end of lower portion 82 adjacent end 42b defines an outward projection 86. Preferably, the transition between lower portion 82 and outward projection 86 defines a circular fillet 88. The upper and lower edges of upper portion 80 and the lower edge of lower portion 82 are preferably rounded to avoid sharp edges which may potentially damage adjacent tissue. Upper portion 80 defines a channel 90 extending laterally therethrough and opening onto first end 42a for receiving spinal rod 14 therethrough. Channel 90 intersects longitudinal passage 40 and is aligned generally perpendicular to longitudinal axis L. Upper and lower portions 80, 82 define a first slot 92, extending from channel 90 toward second end 42b. First slot 92 includes a base portion 94 extending from channel 90 and transitioning into a forked portion 96 having first and second prongs 98a, 98b. Lower portion 82 defines a second slot 100 extending from second end 42b toward first end 42a and being at least partially disposed between prongs 98a, 98b. Further details regarding coupling element 18, including further discussion regarding the structure and operation of first and second slots 92, 100, are disclosed in U.S. patent application Ser. No. 09/408,197, filed on the same day as the subject application and entitled "Advanced Coupling Device Using Shape-Memory Technology".

Figure 8:
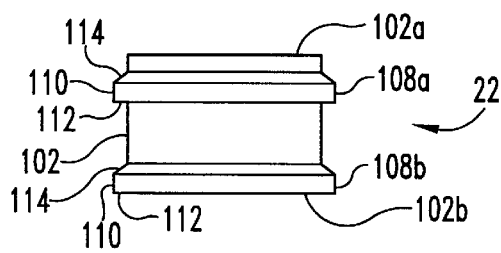
FIG. 8 is a side elevation view of one embodiment of a blocking element for use with the system depicted in FIG. 1.
Figure 9:
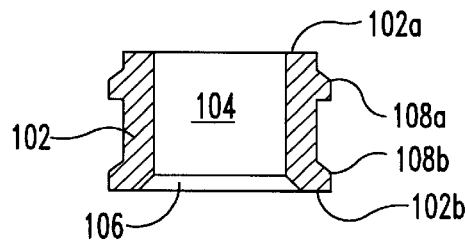
FIG. 9 is a side cross-sectional view of the blocking element shown in FIG. 8.

Referring now to FIGS. 8 and 9, shown therein are various structural details regarding blocking element 22. Blocking element 22 has a generally cylindrical shape and includes a side wall 102 extending between a first end 102a and a second end 102b. Side wall 102 defines a passage 104 extending therethrough including an outwardly tapering portion 106 opening onto second end 102b. Side wall 102 also defines a pair of radial projections or splines 108a, 108b, each having a shape configured substantially complementary to radial grooves 48a, 48b, respectively. More specifically, each of radial projections 108a, 108b includes a circumferential surface 110, an annular surface 112, and a peripheral angular surface 114, respectively corresponding to circumferential surface 50, annular surface 52, and peripheral angular surface 54 of radial grooves 48a, 48b.

Figure 10:
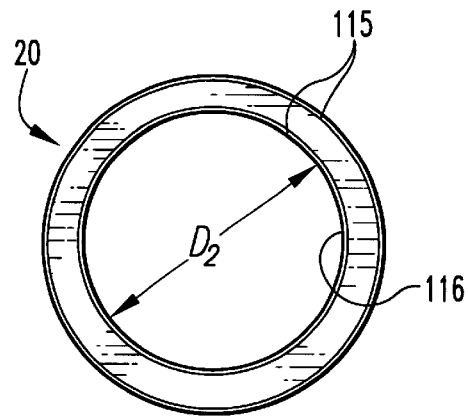
FIG. 10 is a top view of one embodiment of a shape-memory ring used with the system depicted in FIG. 1.

Referring to FIG. 10, shown therein are various structural details regarding locking elements 20. Each of locking elements 20 are generally ring-shaped and preferably have chamfered inner and outer edges 115. Locking elements 20 are at least partially formed of a shape-memory material such as, for example, Nitinol®. Locking elements 20 have an inner surface 116 defining an inner diameter $D_2$ when the shape-memory material is at a temperature below $A_s$. In this state, inner diameter $D_2$ is slightly larger than outer diameter $D_1$ of lower portion 82 of coupling element 18. When the temperature of the shape-memory material is increased above $A_s$, locking element 20 will begin to recover or reform towards its "memorized" configuration. In other words, at temperature $A_s$, inner diameter $D_2$ of locking elements 20 will begin to contract. It should be understood that while locking elements 20 are depicted as circular rings, other shapes and configurations are also contemplated as would occur to one of ordinary skill in the art. Further details regarding the structure and operation of locking elements 20 are disclosed in U.S. patent application Ser. No.09/408,197, filed on the same day as the subject application and entitled "Advanced Coupling Device Using Shape-Memory Technology".

In an alternative embodiment of locking elements 20, the shape-memory material within locking elements 20 displays a stress-induced martensite behavior. In a stress-induced martensitic state, the inner diameter $D_2$ of locking elements 20 is aproximately equal to the outer diameter $D_1$ of lower portion 82 of coupling element 18. However, when the stress is removed from locking elements 20, each of locking elements 20 will recover or reform toward their unstressed or "memorized" configuration, and inner diameter $D_2$ of locking elements 20 will contract.

Referring once again to FIG. 2, shown therein is an initial configuration of coupling device 16. Head 28 of bone screw 12 is positioned within passage 40 of coupling element 18 adjacent radial recess 57, and connecting portion 38 of spinal rod 14 is positioned within the upper portion of channel 90 of coupling element 18. Blocking element 22 is positioned within passage 40 between upper surface 32 of head 28 and spinal rod 14, with circumferential surfaces 110 of radial segments 108a, 108b engaging adjacent inner surface 46 of slot 44 just above first and second radial grooves 48a, 48b, respectively. A plurality of locking elements 20 are disposed about lower portion 82 of coupling element 18 and positioned between upper portion 80 and outward projection 86. Locking elements 20 are initially assembled onto coupling element 18 by biasing lower portion 82 inwardly so that locking elements 20 can be positioned over outward projection 86. When the biasing force is released, lower portion 82 is allowed to return to its undeformed shape and locking elements 20 will be provisionally maintained on lower portion 82. It should be understood that locking elements 20 could alternatively be combined into a single locking element 20 having a thickness approximately equal to the distance between upper portion 80 and outward projection 86. Further details regarding the assembly of system 10, as well as the introduction of system 10 into the surgical site, are disclosed in U.S. patent application Ser. No. 09/408,197, filed on the same day as the subject application and entitled "Advanced Coupling Device Using Shape-Memory Technology".

In the initial configuration of coupling device 16 illustrated in FIG. 2, head 28 of bone screw 12 is loosely received within radial recess 57 such that the angular alignment of bone screw 12 may be variably adjusted. Similarly, connecting portion 38 of spinal rod 14 is loosely received within channel 90 such that spinal rod 14 may be rotated and translated within channel 90. Shortly after system 10 is introduced into the surgical site, the temperature of locking elements 20, and more specifically the shape-memory material contained therein, will begin to rise in response to the conduction of body heat. Once the temperature of locking elements 20 rises to $A_s$, the shape-memory material will begin to enter the austenitic state, and the locking elements 20 will begin to recover or reform toward their "memorized" shape. As this occurs, inner surface 116 of each locking element 20 will exert a compressive force onto lower portion 82 of coupling element 18. However, blocking element 22 will absorb or counter the inward forces exerted by locking elements 20, thus preventing coupling device 16 from reforming and locking bone screw 12 and spinal rod 14 into position relative to coupling element 18. More specifically, blocking element 22 is positioned within passage 40 so that circumferential bearing surfaces 110 of radial segments 108a, 108b engage inner bearing surface 46 and exert an outward force onto coupling element 18 that is equal to the inward compressive forces exerted on coupling element 18 by locking elements 20.

After sufficient passage of time, the temperature of locking elements 20 may eventually rise above $A_f$, which is preferably below normal body temperature, and the shape-memory material will be completely transformed into austenite. At this point, the compressive forces exerted by locking elements 20 are at a maximum. However, blocking element 22 will continue to absorb the compressive forces exerted by locking elements 20 via the abutment of bearing surfaces 110 against inner surface 46. As long as blocking element 22 remains in the position shown in FIG. 2, the surgeon will be able to adjust the angular alignment of bone screw 12 relative to longitudinal axis L and rotate and translate spinal rod 14 within channel 90. Accordingly, it can be seen that blocking element 22 will prevent coupling element 18 from locking or clamping down onto bone screw 12 and spinal rod 14 at temperatures which may exceed $A_f$, thus allowing for the continued manipulation of the position and orientation of bone screw 12 and spinal rod 14 relative to coupling element 18.

Referring now to FIG. 3, once the surgeon has manipulated bone screw 12 and spinal rod 14 into their final orientations and positions relative to coupling element 18, blocking element 22 is displaced from its initial engaged position (shown in FIG. 2) toward head 28 of bone screw 12 by exerting a downward force onto spinal rod 14. In turn, spinal rod 14 contacts end 102a of blocking element 22 and displaces blocking element 22 in a downward direction generally along longitudinal axis L. As blocking element 22 is downwardly displaced within slot 44, circumferential surfaces 110 of radial segments 108a, 108b will slidably engage inner surface 46 of slot 44, and eventually will disengage inner surfaces 46 when radial projections 108a, 108b are at least partially positioned within radial grooves 48a, 48b. The removal of the outward force exerted by blocking element 22 onto coupling element 18 allows locking elements 20 to recover or reform toward their "memorized" shape. The accumulated, internal forces within locking elements 20 result in a reduction in $D_2$ and the contraction of inner surface 116 about coupling element 18. Consequently, the shape of coupling element 18 will also be reformed, and as blocking element 22 is further downwardly displaced, angular surfaces 114 of radial segments 108a, 108b will slide along angular surfaces 54 of radial grooves 48a, 48b until radial segments 108a, 108b are positioned within radial grooves 48a, 48b, respectively. When annular surfaces 112 of radial segments 108a, 108b abut corresponding annular surfaces 52 of radial grooves 48a, 48b, blocking element 22 will be restrained from further downward displacement.

In the final configuration of coupling device 16 shown in FIG. 3, blocking element 22 is positioned within passage 40 so that bearing surfaces 110 will no longer engage inner surface 46 of coupling element 18. As a result, the compressive forces exerted by locking elements 20 will cause coupling element 18 to reform and contract tightly about head 28 of bone screw 12 and connecting portion 38 of spinal rod 14, thus locking bone screw 12 and spinal rod 14 into position relative to coupling element 18 and limiting relative movement therebetween. More specifically, connection portion 38 of spinal rod 14 is clamped within channel 90, and head 28 of bone screw 12 is clamped between circular upper and lower edges 64, 66 of radial recess 57. In this final configuration of system 10, second end 102b of blocking element 22 is shown positioned proximately adjacent top surface 32 of bone screw 12. Although bone screw 12 is shown aligned with longitudinal axis L, even if bone screw 12 had been placed in an angular orientation, head 28 would not interfere with the downward displacement of blocking element 22 because head 28 would be at least partially received within outwardly tapering portion 106 of blocking element 22. It can also be seen that the final position of blocking element 22 does not interfere with the complete engagement of spinal rod 14 within channel 90.

If it becomes necessary to loosen coupling system 10 to allow for the repositioning of bone screw 12 or spinal rod 14 relative to coupling 18, or to allow for the removal of coupling system 10 from the surgical site, locking elements 20 can be cooled until the shape-memory material returns to its martensitic state. As the temperature of locking elements 20 is reduced below $M_s$, inner diameter $D_2$ will begin to increase as locking elements 20 begin to assume their deformed shape. As a result, the grip of coupling element 18 on head 28 of bone screw 12 and connecting portion 38 of spinal rod 14 will loosen, once again allowing bone screw 12 and spinal rod 14 to be manipulated relative to coupling element 18 or entirely removed from coupling element 18.

It should now be understood that the present invention is operable to selectively prevent the premature locking of coupling system 10 to allow for the continued manipulation of bone screw 10 and spinal rod 14 relative to coupling element 18, even at temperatures above $A_f$. In one embodiment of the present invention, the $A_f$ temperature of the shape-memory material within locking elements 20 is below normal body temperature. In another embodiment, the $A_f$ temperature is below ambient room temperature (about 23 degrees Celcius). In this embodiment, at room temperature, locking elements 20 will exert a compressive force onto coupling element 18, which in turn will clamp blocking element 22 in a desired position within passage 40 (see FIG. 2). In this manner, coupling element 18, locking elements 20, and blocking element 22 form a unitary assembly which can be easily manipulated prior to and during a surgical procedure, thus eliminating, or at least reducing "fiddle factor" during surgery. Additionally, by selecting an $A_f$ temperature well below normal body temperature, the recovery of the compressive forces generated by locking elements 20 are maximized by ensuring that the $A_f$ temperature is in fact reached. Moreover, the selection of an $A_f$ temperature well below normal body temperature minimizes the risk of the coupling system loosening up if the temperature of the shape-memory material falls below the $M_s$ temperature.

Although the downward displacement of blocking element 22 within longitudinal passage 40 is brought about by applying a downward force onto spinal rod 14, it should be understood that blocking element 22 can be displaced by other methods as well. For instance, blocking element 22 could alternatively be displaced by an appropriately designed instrument configured to engage a portion of blocking element 22 and apply a downward force thereon. Also, blocking element 22 need not necessarily be downwardly displaced to effect the release of the outward force of blocking element 22 onto inner surface 46 of coupling element 18. For example, blocking element 22 could alternative be upwardly displaced toward first end 42 of coupling element 18 by applying an upward force onto blocking element 22 by way of bone screw 12 or an appropriately designed instrument.

The present invention contemplates any means for selectively preventing the locking of coupling system 10, even at temperatures which may exceed $A_f$, such as would occur to one of ordinary skill in the art. For example, the use of a blocking element at least partially composed of a shape-memory material, having an $A_f$ temperature somewhat above the $A_f$ temperature of coupling elements 20, is also contemplated. In one state, the blocking element would prevent the locking of coupling system 10 at temperatures above the $A_f$ of coupling elements 20. However, in another state, the blocking element would be reformed into a memorized shape at a temperature above its own $A_f$ that would allow locking elements 20 to lock coupling system 10. Preferably, the $A_f$ temperature of the blocking element would be somewhat above normal body temperature so as to avoid the inadvertent locking of coupling system 10 during surgery. In this manner, the temperature of the blocking element could be increased by applying an external heat source so as to give the surgeon the ability to selectively lock coupling system 10 into a desired position at any point in time during surgery, regardless of how long coupling system 10 has resided within the body.

Although one function of the blocking element has been illustrated and described as absorbing or countering the inward forces exerted by a coupling device, it should be understood that the blocking element could alternatively be configured to absorb or counter outward forces so as to selectively prevent the locking of a coupling system. For example, if the shape-memory material within the coupling device were configured to expand upon a sufficient change in temperature to lock a coupling system, the blocking element could be configured to impart an inward force onto the coupling device to absorb or counter the outward forces exerted by the coupling device so as to selectively prevent the locking of the coupling system.

It should also be understood that rather than using locking element 20 to provide the compressive forces necessary to clamp bone screw 12 and spinal rod 14 into position relative to coupling element 18, at least a portion of coupling element could alternatively be formed of a shape-memory material. In this manner, coupling element 18 would provide the compressive forces necessary to lock coupling system 10, and locking elements 20 would not be required.

Additionally, as discussed above, the shape-memory material within coupling device 16, and more specifically locking elements 20, could be tailored to exhibit stress-induced martensite characteristics. Importantly, such use of stress-induced martensite would not require a corresponding change in temperature to effect reformation of coupling device 16 toward its original, memorized shape. The shape-memory material would remain in a stress-induced martensitic state when the coupling device is maintained in its first shape or configuration, and at least a portion of the shape-memory material would be transformed to an austenitic state during reformation of the coupling device 16 toward its second shape or configuration. Preferably, the shape-memory material would exhibit stress-induced martensite behavior at aproximately normal body temperature. Further details regarding the use and characteristics of stress-induced martensite are more fully described in U.S. Pat. No. 5,597,378 to Jervis, entitled "Medical Devices Incorporating SIM Alloy Elements", which has been incorporated by reference into the subject application.

While the invention has been illustrated and described in detail in the drawings and foregoing description, the same is to be considered as illustrative and not restrictive in character, it being understood that only the preferred embodiments have been shown and described, and that all changes and modifications that come within the spirit of the invention are desired to be protected.

What is claimed is:

1. A coupling device for connection to a member, comprising:
   a coupling element including means for connecting to the member;
   shape-memory means for limiting relative movement of the member relative to said coupling element; and
   means for selectively preventing said shape-memory means from limiting said relative movement.

2. The device of claim 1 wherein said shape-memory means is reformable from a first configuration that allows said relative movement to a second configuration that limits said relative movement, said preventing means being transitionable from a first state which prevents said shape-memory means from being reformed to said second configuration to a second state which permits said shape-memory means to reform to said second configuration.

3. A coupling system for connection to a member, comprising:
   a coupling device adapted for connection to the member and being at least partially formed of a shape-memory material, said coupling device being reformable from a first configuration to a second configuration, said first configuration allowing relative movement between the member and said coupling device, said second configuration limiting relative movement between the member and said coupling device; and
   a blocking element co-acting with said coupling device to selectively prevent said coupling device from being reformed to said second configuration.

4. The system of claim 3 wherein said blocking element is transitionable from a first state to a second state, said first state preventing said coupling device from reforming to said second configuration, said second state permitting said coupling device to reform to said second configuration.

5. The system of claim 4 wherein said coupling device defines a first bearing surface, and said blocking element defines a second bearing surface, said first and second bearing surfaces being placed in abutment in said first state to prevent said coupling device from reforming to said second configuration.

6. The system of claim 3 wherein said blocking element is displaceable relative to said coupling device between a first position and a second position, said first position preventing said coupling device from reforming to said second configuration, said second position permitting said coupling device to reform to said second configuration.

7. The system of claim wherein said coupling device has a side wall defining at least one recess, said blocking element having a projection defining a bearing surface, said bearing surface abutting said side wall when said blocking element is in said first position, said projection being at least partially positioned within said at least one recess when said blocking element is in said second position.

8. The system of claim 7 wherein said side wall defines a plurality of said at least one recess, said blocking element defining a corresponding plurality of said projections, each of said projections defining a bearing surface, said bearing surfaces abutting said side wall when said blocking element is in said first position, each of said plurality of projections being at least partially positioned within a corresponding recess when said blocking element is in said second position.

9. The system of claim 7 wherein said coupling device defines a passage extending therethrough positioned along an axis, said blocking element being disposed within said passage and displaceable along said axis between said first and second positions.

10. The system of claim 3 wherein one of said coupling device and said blocking element defines a groove portion and another of said coupling device and said blocking element defines a spline portion, said spline portion having a bearing surface adapted to engage a corresponding surface of said one of said coupling device and said blocking element to prevent said coupling device from reforming to said second configuration, said spline portion being at least partially positionable within said groove portion to permit said coupling device to reform to said second configuration.

11. The system of claim 10 wherein said coupling device defines a passage bounded by a side wall, said blocking element being disposed within said passage, said groove portion extending about an inner perimeter of said side wall, said spline portion extending about an outer perimeter of said blocking element.

12. The system of claim 3 wherein said coupling device includes:
   a coupling element; and
   at least one locking element being at least partially formed of a shape-memory material and co-acting with said coupling element to provide said first and second configurations.

13. The system of claim 12 wherein said coupling element defines a passage extending therethrough and bounded by a side wall, said blocking element and a portion of the member being positioned within said passage, said locking element being disposed about a portion of said coupling element and contracting about said coupling element to provide said second configuration, said second configuration compressing said side wall against said portion of the member to limit relative movement between the member and said coupling element.

14. The system of claim 13 wherein said coupling element is adapted for connection to another member, said coupling element defining a channel extending therethrough and aligned transverse and in communication with said passage, a portion of said another member being positioned within said channel, said second configuration of said coupling element compressing said side wall against said portion of said another member to limit relative movement between said another member and said coupling element.

15. The system of claim 14 wherein said blocking element is disposed within said passage between the member and said another member, said blocking element being displaceable along an axis of said coupling device between a first position that prevents said coupling device from reforming to said second configuration and a second position that permits said coupling device to reform to said second configuration, said blocking element being displaced between said first and second positions by correspondingly displacing one of the members.

16. The system of claim 3 wherein said coupling device defines a passage bounded by a side wall, the member being a bone engaging member having a connecting portion defining an at least partially spherical-shaped head and an engaging portion configured to engage a vertebral body, said side wall defining at least one inner annular recess positioned along said passage for receiving said head therein so that the angular alignment of said bone engaging member may be variably adjusted relative to said coupling device when said coupling device is in said first configuration.

17. The system of claim 3 wherein said shape-memory material exhibits a stress-induced martensite behavior, said shape-memory material having a stress-induced martensitic state, said shape-memory material being in said stress-induced martensitic state when said coupling device is maintained in said first configuration.

18. The system of claim 17 wherein said shape-memory material exhibits said stress-induced martensite behavior at normal body temperature.

19. The system of claim 17 wherein at least a portion of said shape-memory material is transformed to an austenitic state during reformation of said coupling device to said second configuration.

20. The system of claim 3 wherein said shape-memory material has an $A_f$ temperature that is below normal body temperature.

21. The system of claim 3 wherein said shape-memory material has an $A_f$ temperature that is below ambient room temperature.

22. A coupling system for connection to a member, comprising:
a connecting device adapted for connection to the member and being formed at least partly from a shape-memory alloy, said connecting device capable of being transformed from one shape to a different shape, said one shape allowing relative movement between the member and said connecting device, said second shape limiting relative movement between the member and said connecting device; and
a restraining element transitionable from a first state to a second state, said first state preventing said connecting device from assuming said second shape, said second state permitting said connecting device to assume said second shape.

23. The system of claim 22 wherein said restraining element is translatable relative to said connecting device between an engaged position and a disengaged position, said engaged position preventing said connecting device from assuming said second shape, said disengaged position permitting said connecting device to assume said second shape.

24. The system of claim 23 wherein one of said connecting device and said restraining element defines a tongue portion, another of said connecting device and said restraining element defining a groove portion, said tongue portion having a bearing surface adapted to slidably engage a corresponding surface of said another of said connecting device and said restraining element when in said engaged position, said tongue portion being at least partially positioned within said groove portion when in said disengaged position.

25. The system of claim 24 wherein said connecting device defines a passage bounded by a side wall, said blocking element being disposed within said passage, said groove portion extending about an inner perimeter of said side wall, said tongue portion extending about an outer perimeter of said blocking element.

26. The system of claim 23 wherein said connecting device defines an axis, said restraining element being displaceable along said axis between said engaged and disengaged positions.

27. The system of claim 22 wherein said connecting device includes:
a coupling element; and
at least one locking element being at least partially formed of a shape-memory material and being disposed about a portion of said coupling element, said at least one locking element contracting about said coupling element to provide said second shape.

28. The system of claim 24 wherein said connecting device includes a plurality of said at least one locking element, each being disposed about a portion of said coupling element.

29. A coupling system for connection to a member, comprising:
a coupling element defining a passage sized to receive a portion of the member therein;
at least one locking element formed at least partly of a shape-memory alloy and disposed about at least a portion of said coupling element, said at least one locking element capable of being reformed from a first configuration to a second configuration, said first configuration co-acting with said coupling element to allow relative movement between the member and said coupling element, said second configuration co-acting with said coupling element to limit relative movement between the member and said coupling element; and
a blocking element disposed within said passage and transitionable between a first state and a second state, said first state preventing said locking element from assuming said second configuration, said second state permitting said coupling device to assume said second configuration.

30. The system of claims 29 wherein said passage is bounded by a side wall, said side wall defining a first bearing surface, said blocking element defining a second bearing surface, said first and second bearing surfaces being placed in abutment in said first state to prevent said at least one locking element from assuming said second configuration.

31. The system of claim 30 wherein side wall defines at least one recess disposed along said passage, said blocking element having at least one projection defining said second bearing surface, said at least one projection being at least partially positioned within said at least one recess in said second state to allow said locking element to assume said second configuration.

32. A method, comprising:
providing a coupling device adapted to be connected to a member, the coupling device being at least partially formed of a shape-memory material and capable of being reformed from a first shape to a different second shape;
providing a blocking element positioned adjacent the coupling device;
preventing the coupling device from reforming toward its second shape through co-action between the coupling device and a first state of the blocking element to allow relative movement between the member and the coupling device; and
transitioning the blocking element from the first state to a second state to permit the coupling device to reform toward its second shape and limit relative movement between the member and the coupling device.

33. The method of claim 32 wherein the transitioning of the blocking element from the first state to the second state includes displacing the blocking element relative to the coupling device between an engaged position wherein a portion of the blocking element abuts a corresponding portion of the coupling element and a disengaged position wherein the portion of the blocking element no longer abuts the corresponding portion of the coupling element.

34. The method of claim 32 further comprising manipulating the member to a desired position and orientation relative to the coupling device when the blocking element is in the first state.

35. The method of claim 32 wherein the coupling device includes:
a coupling element; and
at least one locking element being at least partially formed of a shape-memory material and co-acting with the coupling element to provide the first and second shapes.

* * * * *

UNITED STATES PATENT AND TRADEMARK OFFICE
CERTIFICATE OF CORRECTION

PATENT NO. : 6,273,888 B1  Page 1 of 1
DATED : August 14, 2001
INVENTOR(S) : Jeff R. Justis It is certified that error appears in the above-identified patent and that said Letters Patent is hereby corrected as shown below:

Column 12,
Line 27, please insert -- 6 -- between "claim" and "wherein".

Signed and Sealed this

Twenty-seventh Day of August, 2002

Attest:

Attesting Officer

JAMES E. ROGAN
Director of the United States Patent and Trademark Office